United States Patent
Cohen et al.

[11] Patent Number: 6,087,553
[45] Date of Patent: Jul. 11, 2000

[54] IMPLANTABLE METALLIC OPEN-CELLED LATTICE/POLYETHYLENE COMPOSITE MATERIAL AND DEVICES

[75] Inventors: Robert C. Cohen, Rockaway Township; Makoto Takeuchi, Ridgewood, both of N.J.

[73] Assignee: Implex Corporation, Allendale, N.J.

[21] Appl. No.: 08/968,917

[22] Filed: Nov. 6, 1997

Related U.S. Application Data

[63] Continuation of application No. 08/607,328, Feb. 26, 1996, abandoned.

[51] Int. Cl.[7] .................................................... A61F 2/28
[52] U.S. Cl. ................................ 623/16; 623/18; 623/22
[58] Field of Search ............................... 623/11, 16, 18, 623/19, 20, 22, 23; 427/2.26, 2.27

[56] References Cited

U.S. PATENT DOCUMENTS

| | | | |
|---|---|---|---|
| 4,164,794 | 8/1979 | Spector et al. . | |
| 4,479,271 | 10/1984 | Bolesky et al. | 623/16 |
| 4,756,862 | 7/1988 | Spector et al. . | |
| 4,978,355 | 12/1990 | Frey et al. | 623/16 |
| 5,282,861 | 2/1994 | Kaplan | 623/16 |
| 5,290,315 | 3/1994 | DeCarlo, Jr. . | |
| 5,443,512 | 8/1995 | Parr et al. . | |
| 5,443,519 | 8/1995 | Averill et al. . | |
| 5,456,723 | 10/1995 | Steinemann et al. . | |
| 5,669,909 | 9/1997 | Zdeblick et al. | 606/73 |
| 5,755,809 | 5/1998 | Cohen et al. | 606/65 |

OTHER PUBLICATIONS

Specification sheet from PROTEK, Cementless Replacement of the Acetabulum <<Press–fit Cup>>, E. Morscher.

*Primary Examiner*—Michael J. Milano
*Attorney, Agent, or Firm*—Arthur L. Plevy

[57] ABSTRACT

A method for making a composite material for implantation in the body which is able to act as a matrix for the biological ingrowth of bone and is suitable as a bearing surface. The method consists of compression molding the implant by forming to net shape the first material to its desired end device and inserting it into a mold cavity. Polyethylene in is then placed onto the first material, and the mold is subjected to heat and pressure for specific time durations. The end result is polyethylene which is fully interdigitated into the first material to a desired depth which is controlled by temperature, pressure and time constraints. The present method creates an interface between the first material and the polyethylene which is securely fixed and does not allow micro and macro motion between the two materials. The compression molding process optimizes the mechanical and wear properties of the polyethylene, and enables the new material to provide a smooth and frictionless bearing surface on one side of the composite material. The opposite side of the composite material is porous and thus allows for biological ingrowth of new bone or cement interdigitation. The first material provides structural stability, yet allows flexibility and load transfer to improve biological interface characteristics and a more normal bony remodeling that are lacking in other acetabular cups. An acetabular cup constructed with the composite material is also disclosed.

16 Claims, 5 Drawing Sheets

IMPLANTABLE METALLIC OPEN-CELLED LATTICE/POLYETHYLENE COMPOSITE MATERIAL AND DEVICES

RELATED APPLICATIONS

This is a continuation of application Ser. No. 08/607,328, filed on Feb. 26 1996, entitled IMPLANTABLE METALLIC OPEN-CELLED LATTICE/POLYETHYLENE COMPOSITE MATERIAL AND DEVICES, now abandoned.

Reference is made to the following co-pending U.S. patent application Ser. No. 08/476,019 filed on Jun. 7, 1995 by R. C. Cohen et al. and entitled "FEMORAL HEAD CORE CHANNEL FILLING PROSTHESIS". The co-pending application is assigned to the Implex Corporation, the assignee herein.

FIELD OF THE INVENTION

The field of the present invention relates generally to bone prostheses and more particularly to an improved composite material for use in medical implants with bearing interfaces. In addition, the invention relates to implantable devices made with the improved composite material.

BACKGROUND OF THE INVENTION

The deterioration of human bone, whether it be due to various degenerative diseases such as osteoarthritis or through bone and/or joint related injuries, is a continuing problem which has resulted in the development of a wide range of implantable orthopedic devices. The need for such implantable devices has encouraged the medical community to come up with new and better bone and/or joint replacements which attempt to mimic the actual structure and motion of the natural articles, while being both stable in biological environments and durable with regard to the stresses and strains put on them by bodily motions. These implants, although constructed to be as simple as possible, may have a plurality of interacting parts. Through repeated use and even from extended residence in the body, these interacting parts tend to break down, causing pain or discomfort, limiting the effective range of motion of the device, and even requiring the replacement of the implant.

The present invention is concerned with the implant bearing surfaces of these devices and means to secure the material that is used in the construction of these surfaces to the implant. It is these implant bearing surfaces which, because of their intimate contact with each other, must be made as smooth and frictionless as possible, especially in joints that demonstrate the widest range of motion. For example, consider the hip joint which is a ball-and-socket joint and as such has a relatively wide range of motion. The joint is composed of two main members, a rounded femoral head and a cup-like socket or acetabulum located in the pelvis, both of which have surfaces that continually abrade each other as the joint moves. Deterioration of the femoral head and/or acetabulum requires replacement of one or both members using an appropriate prosthetic device. These prosthetic devices have been improved over the years, but in general still lack a smooth and frictionless bearing surface which does not produce debris from ball-and-socket motion along the areas of contact, and secure mounting means that eliminates motion at the interface of the implant shell component and bearing insert.

Current technology provides implant bearing materials which are composed of an ultra high molecular weight polyethylene (UHMWPE) machined component which is anchored into the bone with bone cement. Alternatively, the polyethylene component may be assembled to a solid metallic substrate for bone ingrowth. The problem with these polyethylene components, however, involves their attachment either directly to bone or to prosthetic devices. In the case of an acetabular cup, for example, it has proven to be difficult to develop secure mounting means to attach the polyethylene bearing insert to the shell of the acetabular cup.

Many methods and devices have been developed to improve the fixation of the implant in the body so that the implant and its bearing material become as permanent as possible. For example, in interference fit situations where bone quality and patient criteria constraints are met, the polyethylene component is typically secured by a locking mechanism which is either built into or placed adjunct to the metallic cup. The plastic insert may be secured within the metal cup in a variety of methods which include the use of retaining rings, press fitting or force fitting the plastic insert into the interior of the metal cup and/or thermally fitting the plastic insert into the interior of the metal cup. The metal cup is then secured to the patient's acetabulum in any one of a number of commonly practiced techniques. The problem with this arrangement, however, is that the locking grooves which hold the polyethylene surface to the metal cup typically allow for both micro and macro motion at the interface of the polyethylene/metal which, in turn, can cause debris in and around the polyethylene/metal boundary. This polyethylene debris is known to cause bone lysis and is thus severely damaging to surrounding tissue. Additionally, the solid metal cup offers considerable rigidity to the structure, and can adversely affect the natural remodeling of bone.

Another well known method to secure polyethylene implant bearing materials in the body is through the use of cements such as polymethylmethacrylate that anchor the implant to the remaining bone structure. In these cemented situations, where bone quality or patient limitations may not allow an interference fit device to be stable, this bone cement is used as an immediate implant stabilizer by filling all bone voids and securing the device. However, the fact that the polymethylmethacrylate will not bond directly to polyethylene requires the addition of geometric locking grooves for cement mechanical retention. Also, even for those situations where this cement is useful and appropriate, it has a number of distinct disadvantages including a waiting time necessary for the cement to harden, the release of heat from the hardening process which could damage surrounding tissue, and the fact that the presence of this cement prevents bone ingrowth into the prosthesis.

Yet another way which has been used to improve the permanence of implants in the body is to construct the implants with porous outer surfaces so as to receive an ingrowth of body tissue. These implant devices can be made of either thermoplastics or metallic materials. Examples of prosthetic devices constructed with porous thermoplastics appear in U.S. Pat. Nos. 4,164,794 and 4,756,862 both entitled "PROSTHETIC DEVICES HAVING COATINGS OF SELECTED POROUS BIOENGINEERING THERMOPLASTICS" which were issued to Spector et al. and assigned to the Union Carbide Corporation. These devices are composed of an inner functional component and an outer foamed or sintered porous coating of thermoplastics. The thermoplastic coating provides a region where long-term bone fixation is made possible by tissue ingrowth. An example of a porous metallic implant is described in U.S. Pat. No. 5,456,723 entitled "METALLIC IMPLANT ANCHORABLE TO BONE TISSUE FOR REPLACING A BROKEN OR DISEASED BONE" which was issued to S.

G. Steinemann et al. and assigned to Institut Straumann AG. The metallic implant discussed therein provides a porous outer coating for tissue ingrowth and may be made with a plurality of inert metals such as titanium, zirconium, niobium and tantalum. The micro-roughness provided by an acid etching step provides a heavily pitted surface having a very large surface area which is ideal for tissue ingrowth. An implant device constructed with a combination of metallic/nonmetallic parts is also possible as demonstrated in U.S. Pat. No. 5,443,512 entitled "ORTHOPEDIC IMPLANT DEVICE" which was issued to J. E. Parr et al. and assigned to Zimmer, Inc. This device combines the above-mentioned tissue growth-encouraging advantage of a porous metallic layer with the load stability and flexibility of a polymer core. Moreover, the porous metallic layer is melted into the polymer casing so that adhesion and mechanical interlock are achieved without the aid of bone cements.

While the above-mentioned implants have been used successfully for the replacement of human skeletal parts, they in general do not address the problems associated with bearing interfaces. In order to be both functional at bearing interfaces and suitable for long-term residence in the body, such a device needs one surface that is porous and can incorporate natural bone ingrowth for permanent fixation, and another surface which is smooth and frictionless yet durable enough to withstand years of abrasion without creating debris.

Currently there exists an acetabular cup orthopedic implant device which consists of a screen grid-type metallic material hot pressed to polyethylene. The cementless acetabular press-fit cup is constructed with an outer titanium mesh which is created with superimposed layers of screens having a specific pore size and known porosity volume which are welded together in a parallel arrangement to each other. An inner polyethylene bearing material is hot pressed into the titanium mesh shell to form an acetabular cup. The result is an implant device which has both a rigid outer shell that is capable of incorporating bone ingrowth, and a bearing insert which defines a smooth surface for use with a rounded femoral prosthesis end piece. The hot pressing technique, however, does not optimize the mechanical and wear properties of the polyethylene. This is because the polyethylene cup and the titanium mesh material are made separately and then fixed together in a heating process. Because the heat distribution of the hot pressing technique is not uniform, the polyethylene does not melt uniformly, thus causing surface defects and ultimately damaging the surface characteristics of the bearing interface. In addition, the grid-type metallic material is created with superimposed layers of screens resulting in a material and pore shape that does not accurately mimic the characteristics of natural cancellous bone for optimal natural bone ingrowth.

A recently developed, lightweight, strong, porous metal structure mimicking the microstructure of natural cancellous bone which also acts as a matrix for the incorporation of bone is described in U.S. Pat. No. 5,282,861 entitled "OPEN CELL TANTALUM STRUCTURES FOR CANCELLOUS BONE IMPLANTS AND CELL AND TISSUE RECEPTORS" issued to R. B. Kaplan and assigned to Ultramet. The entire disclosure of the '861 patent is incorporated herein by reference. The material disclosed in the '861 patent is available from the Implex Corporation under the tradename HEDROCEL. This material consists of a three dimensional network of pores which form continuous, uniform channels with no dead ends. The material and has a much lower modulus than a pure metallic implant, and has a significantly better pore size and shape distribution than prior art materials. This intricate network of interconnected pores provides optimal permeability and a high surface area to encourage tissue ingrowth, vascularization, and deposition of new bone, while also allowing for the interdigitation of bone cement for those situations that require it. HEDROCEL, although ideal for the construction of orthopedic implants requiring mechanical integrity (as in load bearing applications), is not suitable for use at implant bearing surfaces unless post-processed to include a layer of material such as polyethylene.

It is, therefore, a primary objective of the present invention to provide a composite material for use in medical implants consisting of a first material that is suitable for bone ingrowth or cement interdigitation and a second material that is suitable for implant bearing surfaces, the interface of the two materials consisting of the second material completely interdigitated into a region of the first material such that the second material remains fixed to the first material and does not create debris.

It is a further object of the present invention to provide an acetabular cup prosthesis constructed with the composite material that substantially overcomes the problems associated with prior art acetabular cups.

SUMMARY OF THE INVENTION

A method for making a composite material for implantation in the body which is able to act as a matrix for the biological ingrowth of bone and is suitable as a bearing surface. The method consists of compression molding the implant by forming to net shape the first material of the composite to its desired end device configuration and inserting it into a mold cavity. A second material consisting of plastic powder in a measured quantity is placed onto the first material, and the mold is subjected to heat and pressure for specific time durations. The end result is a fully consolidated second material which is interdigitated into the first material to a desired depth which is controlled by temperature, pressure and time constraints. The present method creates an interface between the first material and the second material which is securely fixed and does not allow the micro and macro motion between the two materials as seen in prior art composites and devices. The compression molding process optimizes the mechanical and wear properties of the second material, and enables the new material to provide a smooth and frictionless bearing surface on one side of the composite material. The opposite side of the composite material is porous and thus allows for biological ingrowth of new bone or cement interdigitation.

The present invention further includes an acetabular cup formed with the improved composite material.

BRIEF DESCRIPTION OF THE DRAWINGS

In order to better understand the present invention, reference should be made to the following detailed description taken in conjunction with the accompanying drawings wherein.

DETAILED DESCRIPTION OF THE INVENTION

The present invention utilizes the many demonstrated advantages of a metallic open-celled lattice material (such as HEDROCEL) when used as a construction material for prosthetic devices, and adds to it a compression molded polyethylene material which is especially useful for providing an implant bearing surface. The dual advantage provided by the composite metallic open-celled lattice/polyethylene material consists of having one material that can be configured as a bearing surface, the one material being securely fixed to a second material that is capable of promoting the natural ingrowth of bone material. The resulting implant will be able to function for both press-fit and cemented situations. The interface between the two materials, which is created by the compression molding technique, consists of completely interdigitated polyethylene into the metallic open-celled lattice material, thus providing a permanently fixed polyethylene/metallic boarder which will not move and create debris that is harmful to the growth of new bone. In addition, the new dual surfaced composite material may be molded into a plurality of desired end devices, including, but by no means limited to, articulating joint implants and acetabular cups.

Figure 1:
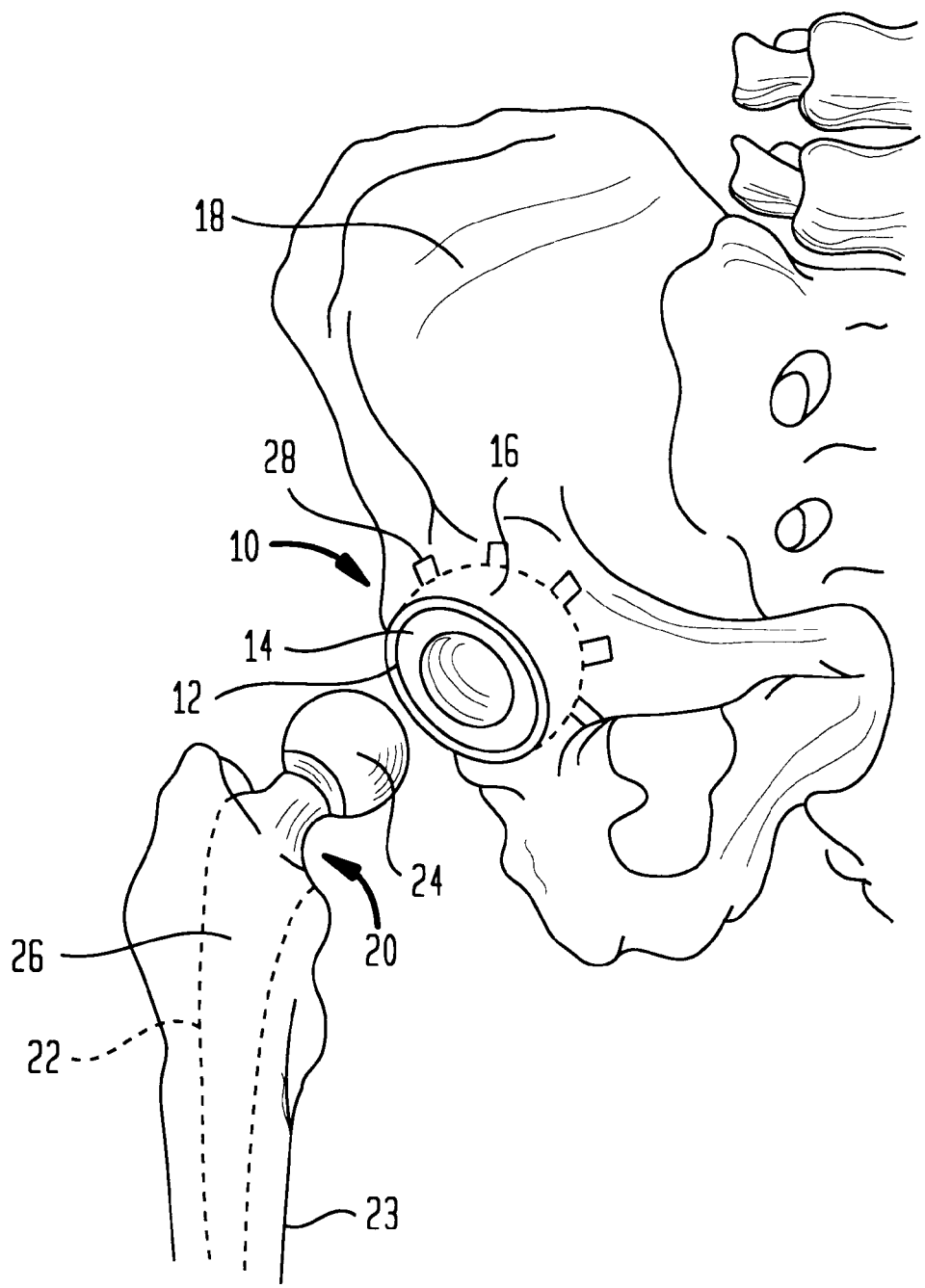
FIG. 1 depicts a perspective view of a prior art acetabular cup and femoral prosthesis.

Referring to FIG. 1 there is shown a prior art total hip replacement consisting of a prosthetic acetabular cup assembly 10 and a femoral prosthesis 20. Generally, the acetabular cup assembly 10 is a two compartment assembly comprising a shell component 12 and a bearing insert 14 which has been assembled within the shell component 12. The shell component 12 is typically made from a metal such as titanium or cobalt-chrome alloy, and may have a porous outer coating 16. The bearing insert 14 is typically made from a plastic material such as polyethylene or ultra high molecular weight polyethylene (UHMWPE), but may in fact be any biocompatible material which has sufficient strength and wear resistance to withstand the pressures and abrasive nature of the joint. The bearing insert 14 is typically held in the shell component 12 by a series of locking grooves or notches (not shown). The entire acetabular cup assembly 10 is also typically attached to the patient's hip bone 18 by a series of geometric locking grooves or pins 28. Alternatively, in interference fit situations where bone quality and patient criteria constraints are met, the acetabular cup may be driven into the patient's acetabulum with a proper impaction tool and may not require fixing pins. The femoral prosthesis end 20 generally consists of a radial femoral stem section 22 and a rounded femoral cap 24. The stem section 22 is inserted into the interior of the femur 23 and may have a porous outer surface 26. The rounded femoral cap and stem are typically composed of an inert metal such as titanium or cobalt-chrome alloy, but any material which is compatible with the bone and body tissues of the patient can, in general, be used. The rounded femoral cap 24 is typically highly polished so as to maintain a smooth and frictionless interface with the bearing surface of the insert 14 of the acetabular cup 10.

Figure 2:
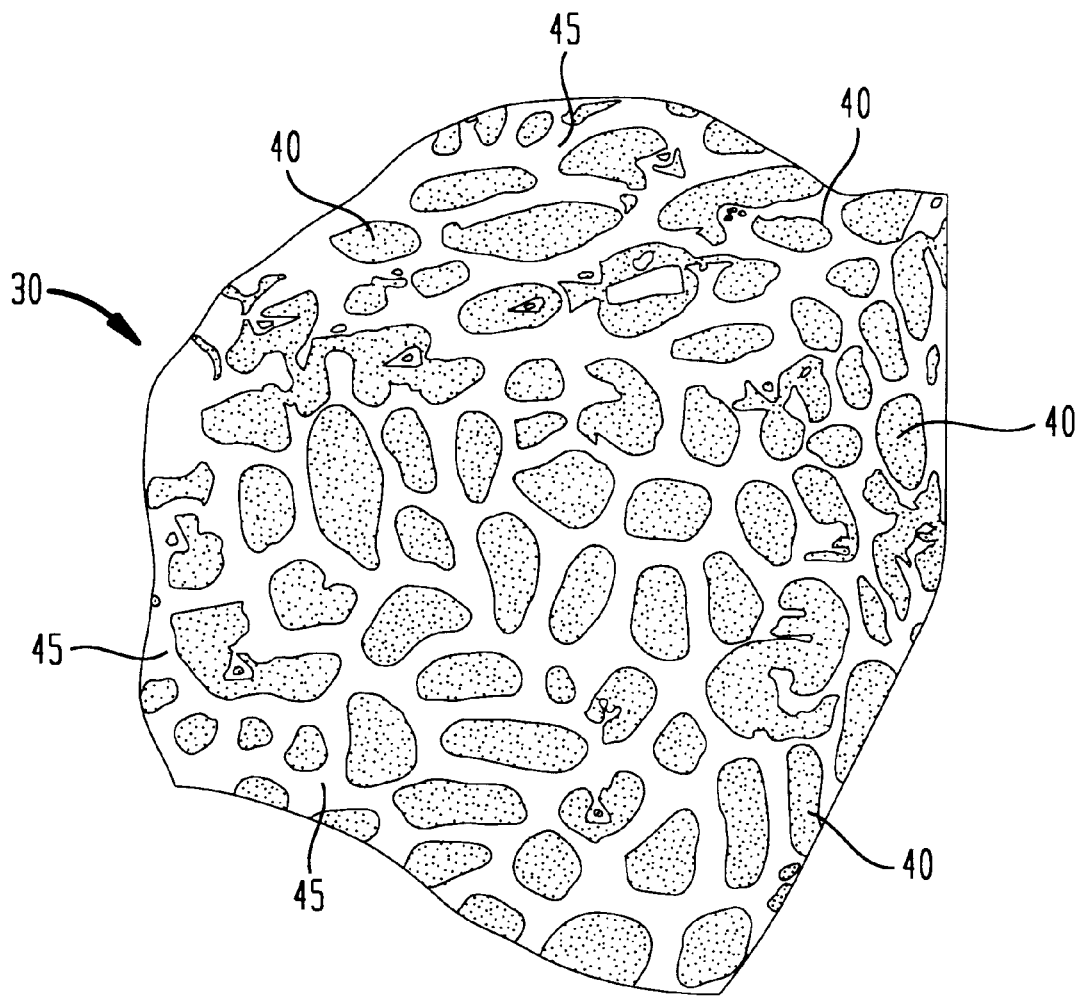
FIG. 2 depicts a perspective view of the metallic open-celled lattice material made in accordance with prior art techniques.

Referring now to FIG. 2, there is shown a perspective view of the metallic open-celled lattice material that will be used as one of the two materials in the composite material of the present invention. The structure 30 consists of large open spaces or pores 40 interconnected by ligaments 45. The use of a material having a volume with large pores is important because such a structure is complementary to the microstructure of natural cancellous bone and thus will enable that portion of the prosthesis device which is in contact with the natural cancellous bone to incorporate new bone into the prosthesis. In the preferred embodiment of the present invention, the metallic open-celled lattice material that will be referred to consists of the open-celled lattice tantalum material available from the Implex Corporation under the tradename HEDROCEL. HEDROCEL is a reticulated vitreous carbon foam material having a tantalum metal layer deposited thereon. The vitreous carbon has a substantially rigid structure comprising an interconnected network having interconnecting continuous channels that create a porous microstructure similar to that of cancellous bone. The tantalum metal is deposited on the surface of the vitreous carbon forming a thin layer which provides the carbon foam with the requisite mechanical properties which the carbon foam does not, by itself, possess. Tantalum has a long history of use as an implant material in bone tissues since it possesses good mechanical properties, excellent corrosion resistance, and demonstrated biocompatibility. Other biocompatible metals, however, can also be used if so desired. HEDROCEL has been demonstrated to accommodate tissue ingrowth, revascularization and deposition of new bone within the porous region, operating as a conduit from the healthy, vascularized bone into the prosthetic device. The pores 40 of the structure 30 form a three dimensional network of continuously connected channels which define a bulk volume porosity of approximately 50–90 percent. Such a network provides optimal permeability and a high surface area which are ideal conditions for the growth of new bone.

The present invention is concerned with modifying one surface of the metallic open-celled lattice material so that a new composite material that can be used, for example, in acetabular cups is attainable. This modification is accomplished in the present invention through the use of a compression molding technique which utilizes the metallic open-celled lattice material as a base material and polymerized polyethylene as a bearing material. The process of compression molding is well known to those skilled in the art, and in the present invention consists of forming the metallic open-celled lattice material into net shape and inserting it into one end of a mold cavity. Powdered polyethylene in a measured quantity is then placed onto the metallic open-celled lattice material and the mold is closed. The cavity is then subjected to heat and pressure for specific time durations depending upon the mass and geometry of the implant device to be constructed. The end result provides a composite material where the interface between the two materials that form the composite is a fully consolidated polyethylene layer that extends into the metallic open-celled lattice material to a depth of approximately 1–3 mm, and a construct which is completely at or near net shape. When compression molding polyethylene, temperatures of around 250° C. and pressures in the neighborhood of 1000 psi are typically required. It should be understood, however, that the exact temperature, pressure and time duration needed to successfully incorporate a given amount of polyethylene into the metallic open-celled lattice material may vary significantly depending on the size, shape and structure of the implant device. In addition, the desired depth of the polyethylene intercalation into the metallic open-celled lattice material may be varied according to the specifications of the desired end device, requiring modifications in all of the above parameters.

The compression molding technique has a distinct advantage over conventional hot pressing techniques. Because of the carefully controlled heating and pressure schemes in use during the compression molding process, the polyethylene is heated and cooled uniformly throughout the process. Unlike a conventional hot pressing technique which would heat only the surface of the polyethylene to melt it in order to press a metallic grid or foam to it, the carefully controlled compression molding process produces an evenly distributed heating which optimizes the mechanical and wear properties of the polyethylene, resulting in a bearing surface that is not surface or subsurface damaged by regions of improperly heated polyethylene. Such a carefully cured surface is less likely to produce polyethylene debris from abrasion with other prosthetic ends.

Figure 3A:
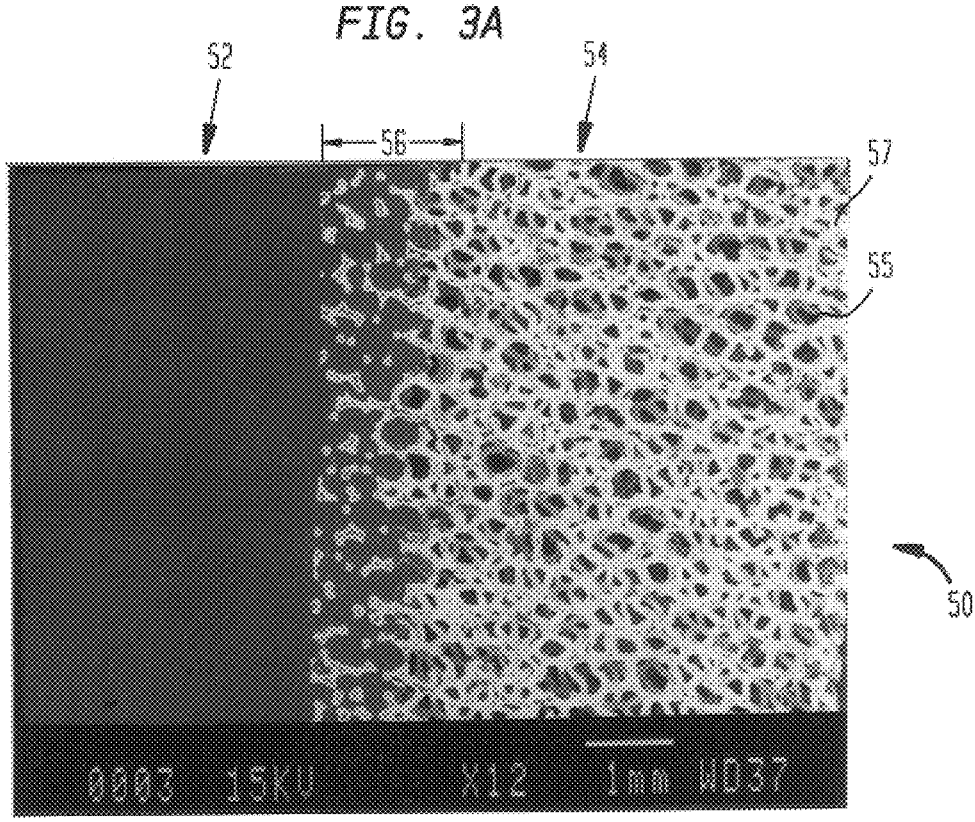
FIGS. 3A–3B are SEM photographs showing the metallic open-celled lattice/polyethylene composite material produced by the compression molding technique.
Figure 3B:
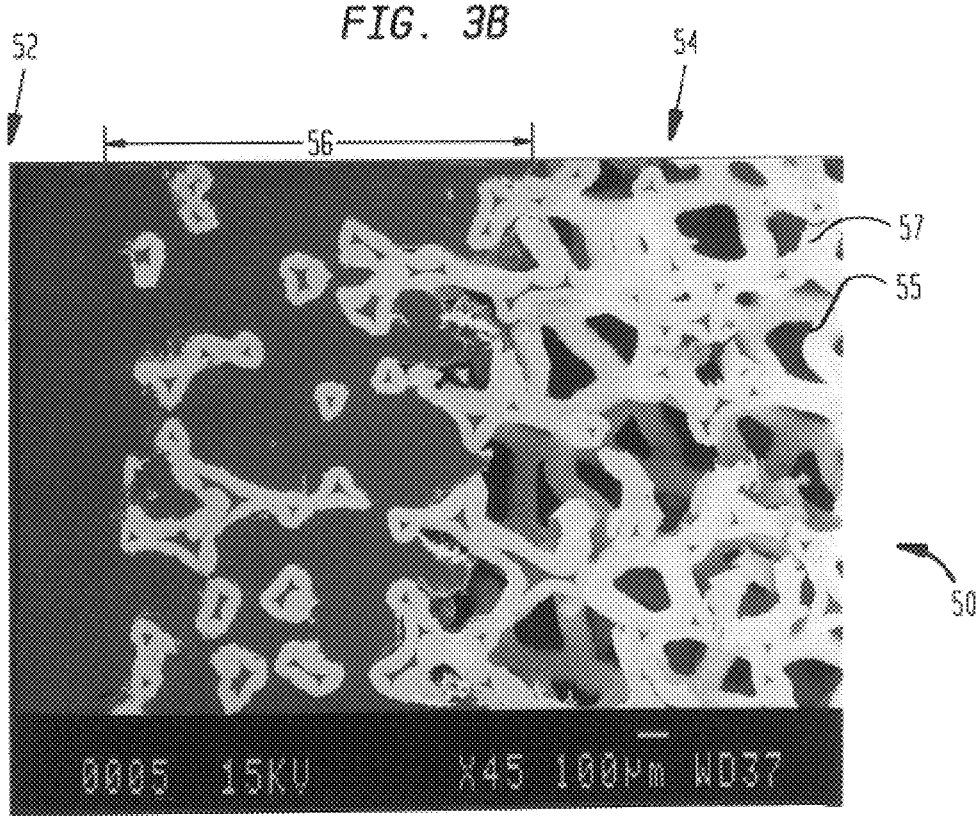

Referring now to FIGS. 3A–3B, there are shown scanning electron microscope (SEM) photographs of the composite metallic open-celled lattice/polyethylene material 50 at 12× (FIG. 3A) and 45× (FIG. 3B) magnification. The dual surfaced composite material depicted therein consists of pure metallic open-celled lattice material 54 and pure polyethylene 52 domains with an interface 56 (consisting of completely interdigitated polyethylene into the metallic open-celled lattice material) formed between the two. Typical penetration thicknesses of the polyethylene into the metallic open-celled lattice material are 1–3 mm. The familiar structure of the metallic open-celled lattice material which consists of interconnected ligaments 57 and open pores 55 is depicted in the figures, but these pores are completely filled with polyethylene in the interface region 56. The interface 56 operates to securely affix the polyethylene material to the metallic open-celled lattice material making motion between the two materials virtually impossible. Given this arrangement, natural cancellous bone can grow into the open porous region of the metallic open-celled lattice material 54 up to the interface region 56 insuring a permanent fixation region for the device in the body.

Figure 4:
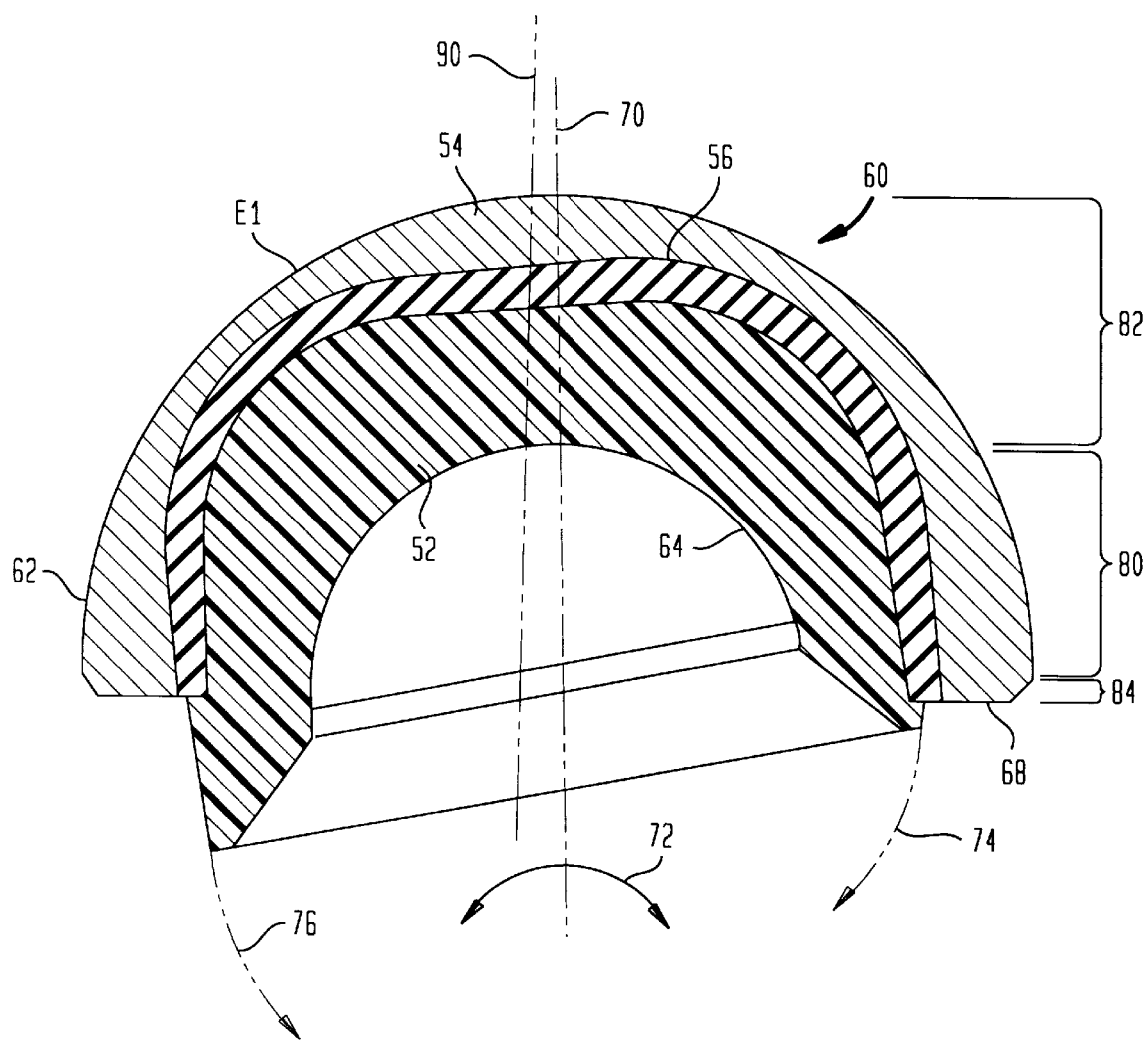
FIG. 4 depicts a cross-sectional view through an acetabular cup prosthesis formed in accordance with the inventive method.

Referring now to FIG. 4, there is shown a cross sectional view through an acetabular cup 60 constructed with the metallic open-celled lattice/polyethylene composite material of the present invention. The acetabular cup depicted therein is modeled after the one disclosed in U.S. Pat. No. 5,443,519 entitled "PROSTHETIC ELLIPSOIDAL ACETABULAR CUP" which was issued to R. G. Averill et al. and assigned to the Implex Corporation, the assignee herein. The entire disclosure of the '519 patent is incorporated herein by reference. Accordingly, the general shape of the acetabular cup depicted in FIG. 4 closely follows the one disclosed in the '519 patent. The acetabular cup of FIG. 4 improves upon the cup shown in the '519 patent by providing a substantially improved technique for attaching the bearing insert to the shell component as will be later explained.

Returning to FIG. 4, the acetabular cup 60 depicted therein is made from the composite material of the present invention consisting of the metallic open-celled lattice material 54, a bearing material 64 consisting of polyethylene 52, and an interface 56 between the two materials consisting of polyethylene completely interdigitated into the metallic open-celled lattice material. The inner concave surface of the bearing material 64 of the acetabular cup 60 is made smooth through a series of well known processing steps familiar to those skilled in the art, and can be molded into a plurality of different faces in order to accommodate a plurality of sizes of femoral ball prostheses (not shown). While the preferred composition of the bearing material is polyethylene (or ultra high molecular weight polyethylene), it should be understood that any material that can provide a substantially smooth and frictionless bearing surface that is also biocompatible and can be compression molded into the metallic open-celled lattice material shell can be used in its place. The exterior surface 62 of the acetabular cup 60 defines a shell-like structure 68 which is contoured and has an apical region 82, a rim region 80 and a small base region 84. The surface curvature of the apical region 82 is ellipsoidal, having a cross-sectional surface curvature that generally follows an elliptical curve E1. The minor axis of the elliptical curve E1 is determined along the mid-axis line 90 while the major axis of the elliptical curve E1 is determined at a perpendicular to the mid-axis line 90, within the plane of the paper. In a preferred embodiment of the shell-like structure 68, the major axis of the elliptical curve E1 is between 0.5 millimeters to 4.0 millimeters larger than the minor axis of the elliptical curve E1, depending upon the size of the acetabulum into which the shell component 68 is to be implanted. Notice should be taken of the fact that the design of the acetabular cup 60, because of the interface 56 created between the metallic open-celled lattice material 54 and the polyethylene 52, does not require locking grooves, notches or pins to hold the polyethylene bearing material 52 to the metallic open-celled lattice shell material 54 as is required in prior art devices. The interface 56 virtually eliminates voids between the metallic open-celled lattice shell material 54 and the polyethylene bearing material 52. The attachment of the bearing material 52 to the shell component 68 is done directly by the compression molding process and does not require the use of cement.

Referring again to FIG. 4, the presently described acetabular cup 60, because of the interface 56 created between the polyethylene bearing material 52 and the metallic open-celled lattice material 54, substantially prevents problems associated with off-set loading which may attempt to move the bearing material 52 relative to the surrounding shell component 68. This off-set loading may be experienced at the implanted acetabular cup as a person undergoes certain movements. These movements are illustrated in FIG. 4 as rotational movements of the bearing material 52 in the directions of the arrows 74,76 or around the mid-axis 70, as indicated by arrow 72. The movement of the bearing material 52 relative to the shell component 68 in the present device is prevented by the entire length of the interface region 56, which is a significant improvement over prior art devices in which locking projections and various angled or inclined surfaces act to hold the bearing insert to the shell component. No matter how well constructed the prior art devices may be, they are prone to at least some movement along the bearing material/shell interface, and this movement is eliminated in the present device.

Figure 5:
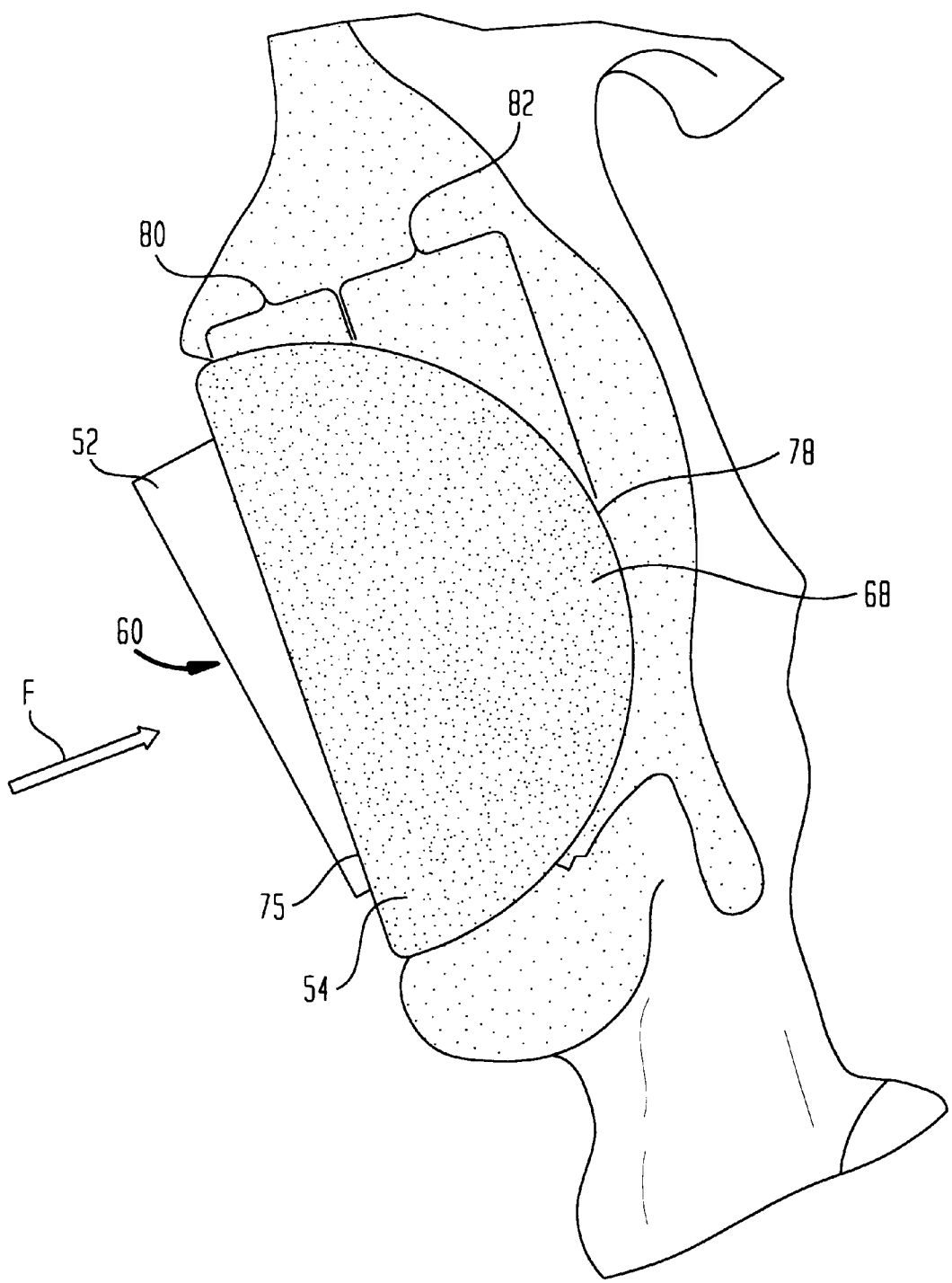
FIG. 5 depicts a cross-sectional view of a patient's prepared acetabulum into which has been inserted the acetabular cup prosthesis of FIG. 4.

Referring now to FIG. 5, the process of implanting the present invention acetabular cup 60 into an acetabulum 78 of a patient will now be described. In FIG. 5, a cross-section of a patient's pelvis is shown in the area of a diseased or damaged acetabulum. The acetabulum 78 depicted therein has been reamed into a spherical shape which has been cut with a spherically-faced rotating reamer using techniques familiar to those skilled in the art. The maximum cross-sectional area measured transversely at the opening of the acetabulum 78 after reaming, is smaller than the maximum cross-sectional area of the shell component 68 to be implanted. The present invention acetabular cup 60 is shown inserted into the acetabulum 78 after it has been reamed into a spherical shape. The acetabular cup 60 is driven into the acetabulum 78 by impacting the acetabular cup 60 with a force F. As the shell component 68 is inserted into the acetabulum 78, the acetabulum distorts to a shape that generally conforms to an ellipsoid. Consequently, as the shell component 68 is inserted into the patient's acetabulum, the shape of the acetabulum 78 is deformed to accommodate the outer contour of the shell component 68 so that the acetabular wall contacts substantially all outer surface portions along the contour thereof while interference forces develop only in the peripheral rim region 80. Since the plastic bearing material 52 is made of a material that is softer than the metallic open-celled lattice material 54 of the shell component 68, the force F needed to insert the acetabular cup 60 into the acetabulum 78 is preferably applied to the base surface 75 of the shell component 68 so not to cause the bearing material 52 to deform.

Returning to FIG. 5, it can be seen that the ellipsoidal curvature of the implanted shell component 68 generally conforms to that of the acetabulum 78 at the respective regions. As a result, minimal or no ejection forces are developed at the interface between the apical surfaces of the shell component and the acetabulum. Advantageously, however, the same ellipsoidal curvature of the shell component provides the interaction of forces between the rim region 80 of the shell component 68 and the rim periphery of the acetabulum needed to produce the desired interference fit.

As noted above, since both the acetabulum 78 and the shell component 68 have corresponding ellipsoidal shapes, the acetabulum 78 engages the shell component 68 across the apical region 82 without applying ejection forces thereto so that the only forces created by the interference fit exist only at the rim region 80 of the shell component 68 within the acetabulum 78.

Following implantation and initial bone ingrowth, the porous end of the metallic open-celled lattice/polyethylene composite material stays where it is placed without retention aids, a reflection of precise contouring and the ingrowth of tissue that prevents dislodgement. The binding between bone and implant stabilizes the implant and prevents loosening. Because of this property, these implants will not need to be permanently held in place by other means such as sutures or cements as required in some prior art devices.

In this way the acetabular cup of the present invention overcomes the problems associated with prior art devices in that it is a dual surfaced implant wherein the interface between the metallic open-celled lattice material and the polyethylene material remains fixed thus preventing debris from forming between these two materials. The device is also constructed so as to receive an ingrowth of new bone using an metallic open-celled lattice material which has been proven to demonstrate this capability in prior art devices. The metallic open-celled lattice material provides structural stability yet allows flexibility and load transfer to improve biological interface characteristics an a more normal bony remodeling that are lacking in other acetabular cups. Further, the compression molding technique used in the construction of the implant optimizes the mechanical and wear properties of the polyethylene material, thereby reducing polyethylene debris at the interface of the bearing surface and any prosthetic insert placed therein.

While a preferred embodiment of the present invention is an acetabular cup as discussed herein, the present composite material disclosed in this invention is not limited to uses as acetabular cup prostheses, and consequently may be fashioned into a prosthetic implant of any type (including articulating joint implants). Further, while the present acetabular cup invention is particularly suited for press-fit implantation, the present invention is not limited to such, and therefore, embodies implantation in any suitable manner. Further, the compression molding process which produces a polyethylene bearing surface on one side of the metallic open-celled lattice material is not limited to putting this layer on only one surface of the material, but on a plurality of such surfaces as is necessary depending upon the desired end device. It should therefore be understood that the embodiments described herein are merely exemplary and that a person skilled in the art may make reasonable variations and modifications to these embodiments utilizing functionally equivalent elements to those disclosed herein. Any and all such variations and modifications, as well as others which may become apparent to those skilled in the art, are intended to be included within the scope and spirit of the invention as defined by the appended claims.

What is claimed is:

1. A composite material suitable for implantation in the body comprising:
   a first foam portion defining a plurality of pores, said first foam portion having a bulk volume porosity between 50–90%, useful for bone fixation;
   a second biocompatible wear resistant portion which is capable of defining an implant bearing surface; and
   an interface between said first portion and said second portion, said interface comprising a region wherein said second portion is interdigitated into said first portion to a depth between 1–3 mm.

2. The composite material according to claim 1, wherein said pores of said first portion are defined by an open-celled lattice structure of interconnecting continuous channels.

3. The composite material according to claim 2, wherein said open-celled lattice structure is covered by a metallic layer.

4. The composite material according to claim 3, wherein said metallic layer comprises a biocompatible metal.

5. The composite material according to claim 4, wherein said biocompatible metal is tantalum.

6. The composite material according to claim 2, wherein said second biocompatible wear resistant portion is polyethylene.

7. The composite material according to claim 1, wherein said interface between said first portion and said second portion is formed by compression molding.

8. The composite material according to claim 7, wherein said interface eliminates motion between said first portion and said second portion.

9. An articulating joint implant for implantation in the body comprising a composite material, said composite material comprising:
   a first foam portion defining a plurality of pores, said first foam portion having a bulk volume porosity between 50–90%, useful for bone fixation;
   a second biocompatible wear resistant portion which is capable of defining an implant bearing surface; and
   an interface between said first portion and said second portion, said interface comprising a region wherein said second portion is interdigitated into said first portion to a depth between 1–3 mm.

10. The implant comprising a composite material according to claim 9, wherein said pores of said first portion are defined by an open-celled lattice structure of interconnecting continuous channels.

11. The implant comprising a composite material according to claim 10, wherein said open-celled lattice structure is covered by a metallic layer.

12. The implant comprising a composite material according to claim 11, wherein said metallic layer comprises a biocompatible metal.

13. The implant comprising a composite material according to claim 12, wherein said biocompatible metal is tantalum.

14. The implant comprising a composite material according to claim 13, wherein said biocompatible wear resistant material is polyethylene.

15. The implant comprising a composite material according to claim 9, wherein said interface between said first portion and said second portion is formed by compression molding.

16. The implant comprising a composite material according to claim 15, wherein said interface eliminates motion between said first portion and said second portion.

* * * * *